United States Patent [19]

Odum

[11] Patent Number: 4,826,316

[45] Date of Patent: May 2, 1989

[54] RADIATION DETECTION APPARATUS

[75] Inventor: James M. Odum, Eden Prairie, Minn.

[73] Assignee: Detector Electronics Corporation, Minneapolis, Minn.

[21] Appl. No.: 55,538

[22] Filed: May 29, 1987

[51] Int. Cl.$^4$ .................................... G01N 21/88
[52] U.S. Cl. .................................... 356/239; 250/372
[58] Field of Search .................. 356/237, 239; 250/252.1 A, 372, 554; 340/528, 600

[56] References Cited

U.S. PATENT DOCUMENTS 3,952,196  4/1976  Larsen .................... 250/578 X
4,405,234  9/1983  Juaire .................... 356/239
4,547,673 10/1985  Larsen et al. ............ 250/554

FOREIGN PATENT DOCUMENTS 2175686 12/1986 United Kingdom ............ 340/578

Primary Examiner—Davis L. Willis
Assistant Examiner—Matthew W. Koren
Attorney, Agent, or Firm—Paul L. Sjoquist

[57] ABSTRACT

Apparatus for detecting radiation with a light-sensitive radiation receiving tube enclosed in a housing behind a transparent window, the invention including an auxiliary internal light source for testing the optical transmissive properties of the window and including a shielding member between the auxiliary light source and the radiation-receiving tube and a reflective mirror for directing light from the auxiliary light source toward the window for reflection off an external interface surface thereof toward the radiation-receiving tube.

8 Claims, 1 Drawing Sheet

RADIATION DETECTION APPARATUS

FIELD OF THE INVENTION

This invention relates to a radiation-detection apparatus, and in particular to a radiation-detection apparatus having an auxiliary internal light source and light-transmission paths for self-checking the operation of the radiation detector as well as the relative contamination of the transparent window in the housing of the detection apparatus.

BACKGROUND OF THE INVENTION

Various radiation detectors are known in the art, in particular U.S. Pat. No. 3,952,196, issued Apr. 20, 1976, and owned by the assignee of the present invention, discloses a device for determining whether the optical surfaces through which radiation must travel from a potential source of radiation to a radiation detector are free from radiation absorbing material or radiation-blocking material. The device disclosed therein includes an enclosure for commonly housing both the auxiliary light source and the radiation-detector tube, while internally isolating the same from each other, thereby preventing radiation transmission within the housing from the light source to the detector. The patent also discloses a radiation path from the light source outwardly from the housing to a reflective surface or surfaces external of the housing, which surfaces reflect at least some of the radiation back to the detector through the same optical surfaces that other external radiation passes. The patent contemplates external reflective surfaces which either form a part of the outside housing structure, or are remotely located therefrom.

Thus, the prior art device described above, provides a self-checking feature for radiation-detection devices in many applications. However, this device suffers disadvantages which limit its usefulness in particular applications. For example, when the radiation-detection apparatus is placed in a corrosive atmosphere, such as an atmosphere laden with chemically corrosive vapors, the external reflective surfaces tend to suffer therefrom, causing a degradation of their light reflectivity. As a result thereof, the degradation of the reflecting surfaces causes false fault indications and/or indication that the radiation-detection device is inoperative when in fact it continues to function normally in all respects except its self-checking features.

A further radiation-detecting device as seen in U.S. Pat. No. 4,405,234, issued Sept. 20, 1983, and also owned by the assignee of the present invention, discloses a device that eliminates the need for an external reflective surface, and therefore, is operable in corrosive environments. This device takes advantage of the refractive properties of light and employs a beveled glass window element through which light from the auxiliary light source passes and is reflected off the exterior interface surface thereof, to a mirror positioned across the window opposite from the auxiliary light source. The light is then reflected off the mirror toward the radiation detector. However, this device suffers from the disadvantage of the cost involved in the manufacture of the beveled glass window element, which is expensive. Also, the light path requires the precise alignment of the auxiliary light source, window element, mirror and radiation detector.

Accordingly, it would be desirable to provide for a radiation-detection apparatus having a self-contained checking capability, operable in a corrosive or contaminated environment, and to do so at substantially reduced cost.

SUMMARY OF THE INVENTION

The present invention includes an enclosed housing having a non-beveled, flat light-transparent window at one end thereof. A radiation-detection tube is enclosed within the housing, and an auxiliary light source is enclosed within the housing in internal optical isolation with respect to the radiation-detection tube. A mirror is located adjacent the auxiliary light source and positioned at an angle with respect to the window. The mirror is positioned to define a small gap between its distal end proximate the window, and the optical isolation housing.

In operation, light produced by the auxiliary light source is reflected by the mirror through the gap toward the window. A portion of that light is then reflected off the exterior interface surface of the window toward the detection tube. The angle of the mirror to the interface surface and the width of the gap are selected to maximize the amount of light that is ultimately reflected back toward the detection tube.

It is an advantage of the present invention that the auxiliary light source, mirror, window, and detection device are, with respect to successful operation, less sensitive to alignment errors that may result during the assembly thereof than related elements as seen in the device described in U.S. Pat. No. 4,405,234, previously mentioned. In addition, in contrast to such prior art device, the present invention eliminates the need for an expensive, beveled window. As a result of the foregoing, the present invention is less costly to manufacture than that prior art device.

It is an object of the present invention to provide a radiation-detection apparatus having enclosed and protected self-checking elements.

It is another object of the present invention to provide a radiation-detection apparatus having a transparent window for viewing a hazardous radiation area, with means for checking the relative transparency of the window.

It is a further object of the present invention to provide for a radiation-detection apparatus that can operate in corrosive environments.

It is also an object of the present invention that it provide for a radiation-detection apparatus that is simple and inexpensive to manufacture.

DESCRIPTION OF THE PREFERRED EMBODIMENT

Figure 1:
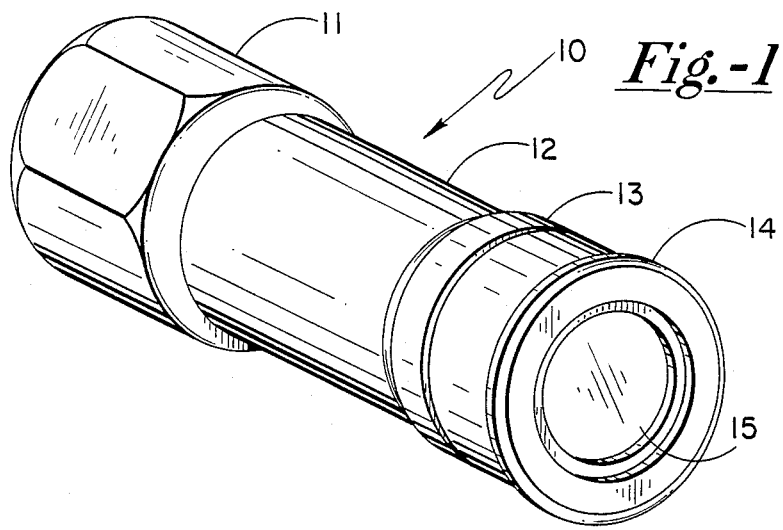
FIG. 1 shows the invention in perspective view.
Figure 3:
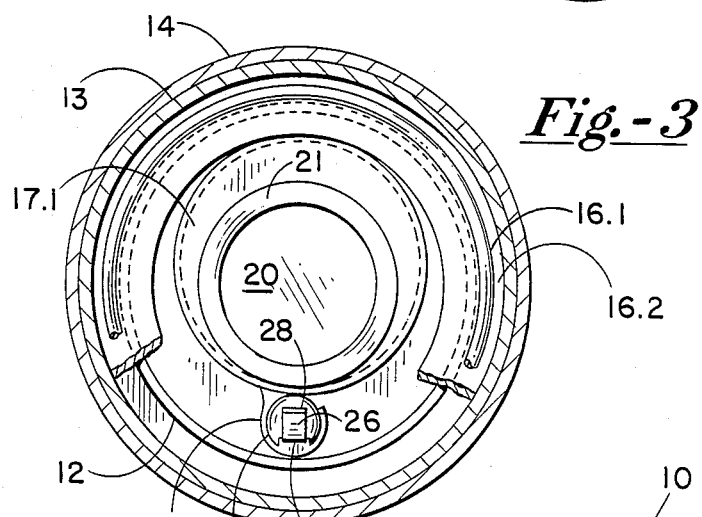
FIG. 3 shows a view taken along lines 3—3 of FIG. 2.

Referring first to FIG. 1, the radiation-detection apparatus 10 is shown in perspective view. A base 11 is adapted for external attachment to a support mechanism, and for securing to housing member 12. A sleeve 13 is threadably attached over the end of housing member 12. A cap 14 is threadably attached to sleeve 13 and clamps window 15 therebetween as more fully understood by referring to FIG. 2.

Figure 2:
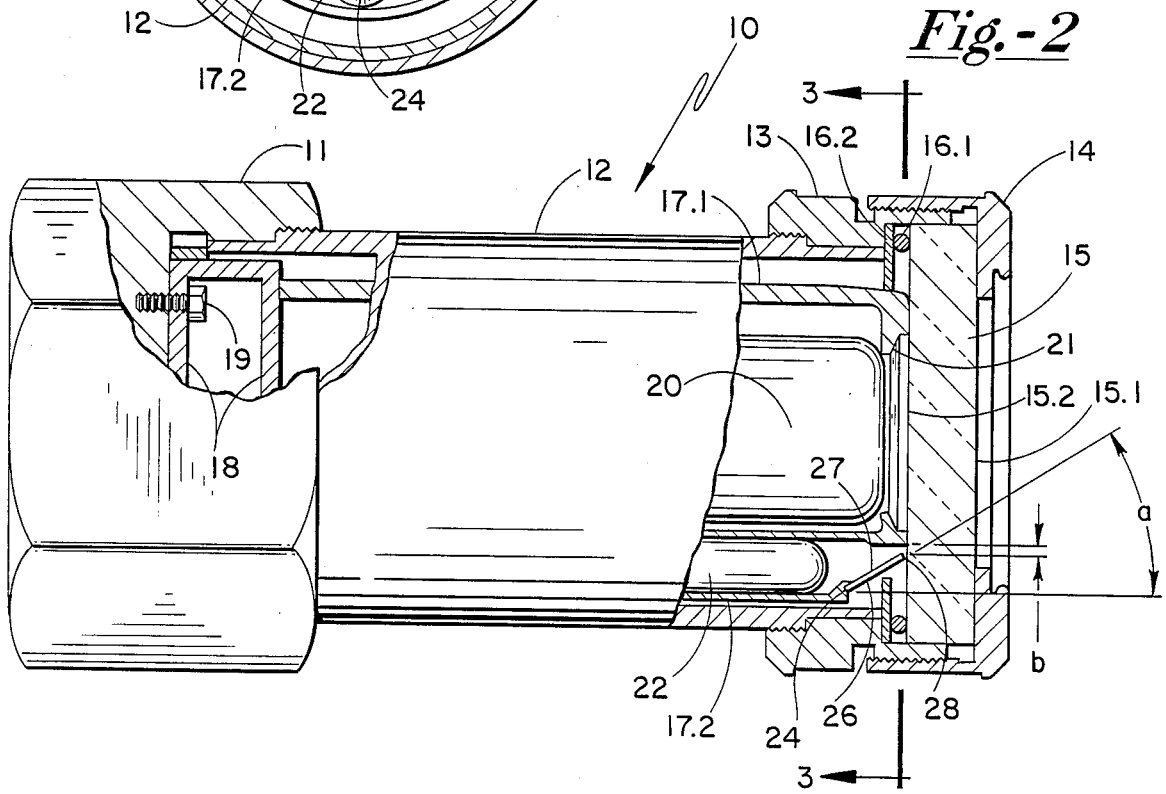
FIG. 2 shows the invention in side view, in partial cross-section.

As seen in more detail in FIG. 2, sleeve 13 is threadably engaged with housing 12 and cap 14 is threadably engaged with sleeve 13 whereby window 15 is clamped between cap 14 and sleeve 13 and rests upon O-ring 16.1 and retaining ring 16.2. Window 15 includes two flat parallel surfaces, exterior interface surface 15.1, and interior surface 15.2. Also, window 15 is optically transparent and is preferably made of fused silica glass. An optical shielding member consisting of a cylindrical detector shield portion 17.1 and a cylindrical auxiliary light source shield portion 17.2, is located within cylindrical housing member 12 and is secured to support 18, which in turn is secured to base 11 by bolts 19.

A radiation-sensitive receiving device, in particular a radiation-detection tube 20 is mounted within shielding portion 17.1 wherein an inwardly extending rim 21 serves to retain detecting tube 20 in proper alignment essentially parallel with the housing member 12. Detection tube 20 is preferably a Geiger-Muller Model Designation DE 1888 tube, sensitive to radiation in the wavelength range of 1,850-2,650 angstroms (A). This wavelength range is characteristic of radiation from a fire source, which is the wavelength range in which the invention is primarily intended to operate.

An auxiliary light source 22 is mounted within shielding portion 17.2. Light source 22 is similar to the light source disclosed in U.S. Pat. No. 4,405,234, consisting of a bulb generating light radiation in the wavelength range of 1,850-2,750 A. Outer shielding portion 17.2 includes a mounting member 24 for securing a reflective mirror 26 adjacent auxiliary tube 22. Reflective mirror 26 includes a reflective surface 27, preferably a highly polished reflective surface capable of reflecting most of the light radiation impinging thereon. As seen in FIG. 2, reflective mirror 26 is mounted at an angle "a" relative to the longitudinal axis of detector 10. A gap "b" is created between the distal end 28 of reflective mirror 26 and the end of shielding portion 17.1 adjacent inner surface 15.2 of window 15.

In operation, detector tube 20 receives light radiation through window 15 from radiation sources lying in the field of view. Since the apparatus in practice is placed in locations where it may have a full field of view of potentially hazardous radiation sources such as fires, detector tube 20 is in a position to sense the radiation as soon as it is generated.

In order that the function and operation of all elements associated with the apparatus may be periodically tested, the auxiliary light source 22 is periodically illuminated. Light produced by source 22 is reflected from reflective surface 27 and is directed thereby through gap "b". A portion of the light that passes through gap "b" will be reflected from interface surface 15.1 toward detection tube 20. Thus, periodic illumination of auxiliary light 22 will result in light being directed toward detection tube 20, and thus, by means of circuits connected to detector tube 20, tube 20 can be monitored to insure that it is operating as expected It was found by experimentation that setting reflective mirror 26 at an "a" angle of 32° served to maximize the amount of light so reflected toward detection tube 20, and thus, insure that the portion of the total light energy produced by light-source 22 that eventually reaches tube 20 will be above the threshhold necessary for tube 20 to detect and signal the presence of ultraviolet radiation. It was also found that reflective mirror 26 could be set at angles of 28° to 35° without significant impairment of the operation of the present invention.

As to operation in a corrosive or contaminated environment, it has been established through experimentation that the amount of radiation lost through window 15 as a result of surface contamination is directly proportional to the amount of light lost through refraction effects at the interface surface 15.1 of window 15. Therefore, the degradation of light from light source 22 to detector tube 20 from such surface contamination is roughly the same as the degradation of radiation received by detector tube 20 through window 15 from external radiation sources. In the event surface 15.1 of window 15 becomes covered by contaminants such as oil or other moist contaminants, such foreign matter will change the index of refraction at the interface surface 15.1. Since the index of refraction of all known and likely contaminants is considerably greater than the index of refraction of air, when the window is contaminated a greater portion of the light emitted from light source 22 will become refracted through interface surface 15.1, and therefore not reflected back toward detector tube 20. This will result in a net reduction in light intensity being received by detector tube 20, which will be recognized as a reduction in electrical signal by the receiving circuits connected to detector tube 20. Such circuits are designed to indicate an alarm condition when this reduction in signal level is detected, and the apparatus will therefore automatically recognize its own impaired ability for radiation detection.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A radiation detection apparatus having facility for self-checking of optical surface contamination, comprising:
    (a) a housing having an opening at one end thereof;
    (b) a radiation-sensitive receiving device in said housing;
    (c) a light-transmissive window mounted in said housing opening, said window having flat parallel surfaces orthogonal to said radiation-sensitive receiving device, including a forward interface surface exposed to contamination;
    (d) an optical shielding member about said receiving device and having an opening facing said window;
    (e) a light source mounted in said housing outside said optical-shielding member adjacent the window; and
    (f) reflective means, for reflecting light produced by the auxiliary light source toward the window for reflection off the forward interface surface thereof toward the radiation-sensitive receiving device, the reflective means being mounted within said housing adjacent the window and disposed at an oblique angle to said forward interface surface, and the reflective means and said optical-shielding member defining a small gap therebetween through which the auxiliary light reflected by the reflective means passes.

2. The apparatus of claim 2, wherein said housing is a cylindrical member about an axis.

3. The apparatus of claim 2, wherein said radiation-sensitive receiving device is mounted along said axis.

4. The apparatus of claim 3, wherein said optical-shielding member is concentrically mounted about said receiving device.

5. The apparatus of claim 2, wherein the reflective means is mounted at an angle in the range of 28°–35° relative to said axis.

6. The apparatus of claim 4, wherein said light-reflective means is mounted to said housing.

7. The apparatus of claim 6, wherein said window is mounted normal to said axis.

8. The apparatus of claim 7, wherein said window is constructed of fused silica.

* * * * *